United States Patent
Casey et al.

(10) Patent No.: US 12,357,384 B2
(45) Date of Patent: *Jul. 15, 2025

(54) SPINAL BALANCE ASSESSMENT

(71) Applicant: NuVasive, Inc., San Diego, CA (US)

(72) Inventors: Niall Casey, San Diego, CA (US); Jennifer Jassawalla, San Diego, CA (US); Eric Forman, San Diego, CA (US); Thomas Scholl, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 909 days.

This patent is subject to a terminal disclaimer.

(21) Appl. No.: 17/531,405

(22) Filed: Nov. 19, 2021

(65) Prior Publication Data
US 2022/0071710 A1     Mar. 10, 2022

Related U.S. Application Data

(63) Continuation of application No. 16/692,209, filed on Nov. 22, 2019, now Pat. No. 11,207,136, which is a continuation of application No. 15/979,395, filed on May 14, 2018, now Pat. No. 10,507,061, which is a continuation of application No. 14/216,411, filed on Mar. 17, 2014, now Pat. No. 9,968,408.

(60) Provisional application No. 61/802,180, filed on Mar. 15, 2013.

(51) Int. Cl.
*A61B 34/10* (2016.01)
*G16H 50/50* (2018.01)

(52) U.S. Cl.
CPC .......... *A61B 34/10* (2016.02); *G16H 50/50* (2018.01); *A61B 2034/105* (2016.02)

(58) Field of Classification Search
CPC ... A61B 34/10; A61B 2034/105; G16H 50/50
See application file for complete search history.

(56) References Cited

U.S. PATENT DOCUMENTS

| | | | |
|---|---|---|---|
| 2,693,798 A | 11/1954 | Haboush |
| 3,866,458 A | 2/1975 | Wagner |
| 4,409,968 A | 10/1983 | Drummond |
| 4,411,259 A | 10/1983 | Drummond |

(Continued)

FOREIGN PATENT DOCUMENTS

| | | |
|---|---|---|
| CA | 2826947 | 3/2014 |
| CN | 2885154 | 4/2007 |

(Continued)

OTHER PUBLICATIONS

Aubin et al., "Preoperative planning simulator for spinal deformity surgeries", Spine, 2008, pp. 2143-2152, 33, No. 20.

(Continued)

*Primary Examiner* — Bijan Mapar

(57) ABSTRACT

The present application describes computer apparatus and software programs useful to the field of corrective spinal surgery. The apparatus and software implement and facilitate methods for assessing the degree of balance and alignment achieved through corrective measures applied to the spine prior to completing a surgical procedure. The apparatus and software facilitate pre-operative planning and virtual testing of the corrective measures to be applied. The apparatus and software further facilitate intra-operative reconciliation with the pre-operative plan prior to completing the surgery.

20 Claims, 6 Drawing Sheets

(56) References Cited

U.S. PATENT DOCUMENTS

| | | |
|---|---|---|
| 4,474,046 A | 10/1984 | Cook |
| 4,653,481 A | 3/1987 | Howland et al. |
| 4,773,402 A | 9/1988 | Asher |
| 4,887,595 A | 12/1989 | Heinig et al. |
| 5,099,846 A | 3/1992 | Hardy |
| 5,113,685 A | 5/1992 | Asher et al. |
| 5,161,404 A | 11/1992 | Hayes |
| 5,239,716 A | 8/1993 | Fisk |
| 5,271,382 A | 12/1993 | Chikama |
| 5,290,289 A | 3/1994 | Sanders et al. |
| 5,389,099 A | 2/1995 | Hartmeister et al. |
| 5,490,409 A | 2/1996 | Weber |
| 5,548,985 A | 8/1996 | Yapp |
| 5,564,302 A | 10/1996 | Watrous |
| 5,591,165 A | 1/1997 | Jackson |
| 5,658,286 A | 8/1997 | Sava |
| 5,672,175 A | 9/1997 | Martin |
| 5,704,937 A | 1/1998 | Martin |
| 5,740,802 A | 4/1998 | Nafis |
| 5,765,561 A | 6/1998 | Chen |
| 5,799,055 A | 8/1998 | Peshkin et al. |
| 5,819,571 A | 10/1998 | Johnson |
| 5,819,580 A | 10/1998 | Gauthier |
| 5,880,976 A | 3/1999 | DiGioia III |
| D415,665 S | 10/1999 | Nordell, II et al. |
| 6,006,581 A | 12/1999 | Holmes |
| 6,015,409 A | 1/2000 | Jackson |
| 6,024,759 A | 2/2000 | Nuss et al. |
| 6,035,691 A | 3/2000 | Lin et al. |
| 6,128,944 A | 10/2000 | Haynes |
| 6,205,411 B1 | 3/2001 | DiGioia, III et al. |
| 6,226,548 B1 | 5/2001 | Foley |
| 6,264,658 B1 | 7/2001 | Lee et al. |
| 6,285,902 B1 | 9/2001 | Kienzle, III |
| 6,327,491 B1 | 12/2001 | Franklin et al. |
| 6,332,780 B1 | 12/2001 | Traxel et al. |
| 6,529,765 B1 | 3/2003 | Franck |
| 6,592,585 B2 | 7/2003 | Lee et al. |
| 6,596,008 B1 | 7/2003 | Kambin |
| 6,644,087 B1 | 11/2003 | Ralph et al. |
| 6,701,174 B1 | 3/2004 | Krause |
| 6,711,432 B1 | 3/2004 | Krause |
| 7,346,382 B2 | 3/2008 | McIntyre et al. |
| 7,454,939 B2 | 11/2008 | Garner et al. |
| 7,488,331 B2 | 2/2009 | Abdelgany |
| 7,634,306 B2 | 12/2009 | Sarin et al. |
| RE42,226 E | 3/2011 | Foley et al. |
| 7,957,831 B2 | 6/2011 | Isaacs |
| 8,101,116 B2 | 1/2012 | Lindh, Sr. et al. |
| 8,126,736 B2 | 2/2012 | Anderson et al. |
| 8,177,843 B2 | 5/2012 | Schalliol |
| 8,235,998 B2 | 8/2012 | Miller et al. |
| 8,255,045 B2 | 8/2012 | Gharib et al. |
| 8,298,242 B2 | 10/2012 | Justis et al. |
| 8,374,673 B2 | 2/2013 | Adcox |
| 8,442,621 B2 | 5/2013 | Gorek et al. |
| 8,459,090 B2 | 6/2013 | Wilcox et al. |
| 8,506,603 B2 | 8/2013 | McClintock et al. |
| 8,549,888 B2 | 10/2013 | Isaacs |
| 8,607,603 B2 | 12/2013 | Justis et al. |
| 8,668,699 B2 | 3/2014 | Thomas et al. |
| 8,714,427 B2 | 5/2014 | McClintock et al. |
| 8,744,826 B2 | 6/2014 | Skalli et al. |
| 8,753,346 B2 | 6/2014 | Suarez et al. |
| 8,770,006 B2 | 7/2014 | Harper |
| 8,831,324 B2 | 9/2014 | Penenberg |
| 8,885,899 B2 | 11/2014 | Illes et al. |
| 8,951,258 B2 | 2/2015 | Peultier |
| 8,983,813 B2 | 3/2015 | Miles et al. |
| 8,992,542 B2 | 3/2015 | Hagag et al. |
| 9,119,670 B2 | 9/2015 | Yang et al. |
| 9,129,054 B2 | 9/2015 | Nawana et al. |
| 9,204,937 B2 | 12/2015 | Edelhauser et al. |
| 9,211,145 B2 | 12/2015 | Pereiro de Lamo et al. |
| 9,233,001 B2 | 1/2016 | Miles et al. |
| 9,248,002 B2 | 2/2016 | McCarthy |
| 9,320,604 B2 | 4/2016 | Miles et al. |
| 9,408,698 B2 | 8/2016 | Miles et al. |
| 9,452,050 B2 | 9/2016 | Miles et al. |
| 9,572,682 B2 | 2/2017 | Aghazadeh |
| 9,597,157 B2 | 3/2017 | Hagag et al. |
| 9,662,228 B2 | 5/2017 | McCarthy |
| 9,700,292 B2 | 7/2017 | Nawana et al. |
| 9,724,167 B2 | 8/2017 | Ziaei et al. |
| 9,757,072 B1 | 9/2017 | Urbalejo |
| 9,785,246 B2 | 10/2017 | Isaacs |
| 9,861,446 B2 | 1/2018 | Lang |
| 9,877,847 B2 | 1/2018 | Bettenga |
| 9,962,166 B1 | 5/2018 | Sachs et al. |
| 9,968,408 B1 | 5/2018 | Casey et al. |
| 10,139,920 B2 | 11/2018 | Isaacs |
| 10,188,480 B2 | 1/2019 | Scholl |
| 10,420,480 B1 | 9/2019 | Schermerhorn |
| 10,444,855 B2 | 10/2019 | Isaacs |
| 10,463,433 B2 | 11/2019 | Turner et al. |
| 10,507,060 B2 | 12/2019 | Casey et al. |
| 10,507,061 B2 | 12/2019 | Casey et al. |
| 10,684,697 B2 | 6/2020 | Isaacs |
| 10,695,099 B2 | 6/2020 | Scholl |
| 10,709,509 B2 | 7/2020 | Scholl |
| 10,987,169 B2 | 4/2021 | Turner et al. |
| 11,207,132 B2 | 12/2021 | Isaacs |
| 11,207,136 B2 | 12/2021 | Casey et al. |
| 11,229,493 B2 | 1/2022 | Finley |
| 11,231,787 B2 | 1/2022 | Isaacs |
| 11,376,045 B2 | 7/2022 | Scholl |
| 2002/0107573 A1 | 8/2002 | Steinberg |
| 2003/0055435 A1 | 3/2003 | Barrick |
| 2003/0055502 A1 | 3/2003 | Lang et al. |
| 2003/0060824 A1 | 3/2003 | Viart |
| 2004/0044295 A1 | 3/2004 | Reinart et al. |
| 2004/0068187 A1 | 4/2004 | Krause et al. |
| 2004/0087962 A1 | 5/2004 | Gorek |
| 2004/0097952 A1 | 5/2004 | Sarin et al. |
| 2004/0144149 A1 | 7/2004 | Strippgen et al. |
| 2004/0147927 A1 | 7/2004 | Tsougarakis et al. |
| 2004/0152972 A1 | 8/2004 | Hunter |
| 2005/0043660 A1 | 2/2005 | Stark et al. |
| 2005/0054917 A1 | 3/2005 | Kitson |
| 2005/0119593 A1 | 6/2005 | Gallard et al. |
| 2005/0192575 A1 | 9/2005 | Pacheo |
| 2005/0203511 A1 | 9/2005 | Wilson-MacDonald et al. |
| 2005/0245817 A1 | 11/2005 | Clayton et al. |
| 2005/0262911 A1 | 12/2005 | Dankowicz et al. |
| 2005/0288809 A1 | 12/2005 | Spaeth et al. |
| 2006/0015030 A1 | 1/2006 | Poulin et al. |
| 2006/0082015 A1 | 4/2006 | Happonen et al. |
| 2006/0150698 A1 | 7/2006 | Garner et al. |
| 2006/0150699 A1 | 7/2006 | Garner et al. |
| 2006/0212158 A1 | 9/2006 | Miller |
| 2006/0235338 A1 | 10/2006 | Pacheco |
| 2006/0235427 A1 | 10/2006 | Thomas et al. |
| 2006/0264973 A1 | 11/2006 | Abdelgany |
| 2007/0073137 A1 | 3/2007 | Schoenefeld |
| 2007/0093689 A1 | 4/2007 | Steinberg |
| 2007/0118055 A1 | 5/2007 | McCombs |
| 2007/0172797 A1 | 7/2007 | Hada |
| 2007/0174769 A1 | 7/2007 | Nycz |
| 2007/0227216 A1 | 10/2007 | Schalliol |
| 2007/0233079 A1 | 10/2007 | Fallin et al. |
| 2007/0269544 A1 | 11/2007 | Erickson et al. |
| 2007/0288064 A1 | 12/2007 | Butson et al. |
| 2008/0009945 A1 | 1/2008 | Pacheco |
| 2008/0039717 A1 | 2/2008 | Frigg et al. |
| 2008/0103500 A1 | 5/2008 | Chao et al. |
| 2008/0161680 A1 | 7/2008 | Von Jako |
| 2008/0177203 A1 | 7/2008 | von Jako |
| 2008/0212858 A1 | 9/2008 | Boese et al. |
| 2008/0262812 A1 | 10/2008 | Arata et al. |
| 2008/0269596 A1 | 10/2008 | Revie et al. |
| 2008/0319275 A1 | 12/2008 | Chiu |
| 2009/0018808 A1 | 1/2009 | Bronstein |
| 2009/0024164 A1 | 1/2009 | Neubardt |
| 2009/0099605 A1 | 4/2009 | Fallin et al. |

(56) References Cited

U.S. PATENT DOCUMENTS

| | | |
|---|---|---|
| 2009/0118714 A1 | 5/2009 | Teodorescu |
| 2009/0132050 A1 | 5/2009 | Holm |
| 2009/0138020 A1 | 5/2009 | Park et al. |
| 2009/0157083 A1 | 6/2009 | Park et al. |
| 2009/0222020 A1 | 9/2009 | Schmuck et al. |
| 2009/0226055 A1 | 9/2009 | Dankowicz et al. |
| 2009/0226068 A1 | 9/2009 | Fitz et al. |
| 2009/0249851 A1 | 10/2009 | Isaacs |
| 2009/0254097 A1 | 10/2009 | Isaacs |
| 2009/0254326 A1 | 10/2009 | Isaacs |
| 2009/0276045 A1 | 11/2009 | Lang |
| 2009/0287271 A1 | 11/2009 | Blum et al. |
| 2009/0299477 A1 | 12/2009 | Clayton et al. |
| 2010/0030232 A1 | 2/2010 | Zehavi et al. |
| 2010/0042105 A1 | 2/2010 | Park et al. |
| 2010/0042154 A1 | 2/2010 | Biedermann et al. |
| 2010/0076563 A1 | 3/2010 | Otto et al. |
| 2010/0100011 A1 | 4/2010 | Roche |
| 2010/0101295 A1 | 4/2010 | Miller et al. |
| 2010/0111631 A1 | 5/2010 | Trieu et al. |
| 2010/0177948 A1 | 7/2010 | Le Bras |
| 2010/0183201 A1 | 7/2010 | Schwab et al. |
| 2010/0191071 A1 | 7/2010 | Anderson et al. |
| 2010/0191100 A1 | 7/2010 | Anderson et al. |
| 2010/0217109 A1 | 8/2010 | Belcher |
| 2010/0268119 A1 | 10/2010 | Morrison |
| 2010/0292963 A1 | 11/2010 | Schroeder |
| 2011/0040340 A1 | 2/2011 | Miller et al. |
| 2011/0054870 A1 | 3/2011 | Dariush et al. |
| 2011/0066193 A1 | 3/2011 | Lang et al. |
| 2011/0071802 A1 | 3/2011 | Bojarski et al. |
| 2011/0084108 A1 | 4/2011 | McClintock et al. |
| 2011/0093108 A1 | 4/2011 | Ashby et al. |
| 2011/0121049 A1 | 5/2011 | Malinouskas |
| 2011/0245871 A1 | 10/2011 | Williams |
| 2011/0253760 A1 | 10/2011 | McClintock et al. |
| 2011/0265538 A1 | 11/2011 | Trieu et al. |
| 2011/0270262 A1 | 11/2011 | Justis et al. |
| 2011/0295378 A1 | 12/2011 | Bojarski et al. |
| 2011/0305379 A1 | 12/2011 | Mahfouz |
| 2011/0319745 A1 | 12/2011 | Frey |
| 2012/0010710 A1 | 1/2012 | Frigg |
| 2012/0014580 A1 | 1/2012 | Blum |
| 2012/0035507 A1 | 2/2012 | George et al. |
| 2012/0041562 A1 | 2/2012 | Shachar et al. |
| 2012/0047980 A1 | 3/2012 | Harper |
| 2012/0116203 A1 | 5/2012 | Vancraen et al. |
| 2012/0141034 A1 | 6/2012 | Iannotti et al. |
| 2012/0186411 A1 | 7/2012 | Lodahi et al. |
| 2012/0230573 A1 | 9/2012 | Ito et al. |
| 2012/0247173 A1 | 10/2012 | Paris et al. |
| 2012/0265268 A1 | 10/2012 | Blum |
| 2012/0274631 A1 | 11/2012 | Friedland et al. |
| 2012/0289965 A1 | 11/2012 | Gelaude et al. |
| 2013/0053854 A1 | 2/2013 | Schoenefeld et al. |
| 2013/0060130 A1 | 3/2013 | Park et al. |
| 2013/0072980 A1 | 3/2013 | Biedermann et al. |
| 2013/0072982 A1 | 3/2013 | Simonson |
| 2013/0091921 A1 | 4/2013 | Wilcox et al. |
| 2013/0096625 A1 | 4/2013 | McClintock et al. |
| 2013/0113791 A1 | 5/2013 | Isaacs |
| 2013/0123850 A1 | 5/2013 | Schoenefeld et al. |
| 2013/0131480 A1 | 5/2013 | Ruhl |
| 2013/0131486 A1 | 5/2013 | Copf et al. |
| 2013/0144342 A1 | 6/2013 | Strauss et al. |
| 2013/0173240 A1 | 7/2013 | Koell et al. |
| 2013/0218163 A1 | 8/2013 | Frey |
| 2013/0296954 A1 | 11/2013 | Skaggs et al. |
| 2013/0303883 A1 | 11/2013 | Zehavi et al. |
| 2013/0304217 A1 | 11/2013 | Reeber et al. |
| 2013/0304429 A1 | 11/2013 | Haimerl |
| 2013/0307955 A1 | 11/2013 | Deitz et al. |
| 2013/0325069 A1 | 12/2013 | Pereiro de Lamo et al. |
| 2013/0345757 A1 | 12/2013 | Stad |
| 2014/0025118 A1 | 1/2014 | Fallin et al. |
| 2014/0031871 A1 | 1/2014 | Fallin et al. |
| 2014/0066994 A1 | 3/2014 | Dominik et al. |
| 2014/0076883 A1 | 3/2014 | Brailovski et al. |
| 2014/0081659 A1 | 3/2014 | Nawana et al. |
| 2014/0100582 A1 | 4/2014 | Koch et al. |
| 2014/0135841 A1 | 5/2014 | Wallenstein |
| 2014/0135842 A1 | 5/2014 | Wallenstein |
| 2014/0135843 A1 | 5/2014 | Barrus |
| 2014/0135844 A1 | 5/2014 | Ark et al. |
| 2014/0137618 A1 | 5/2014 | Isaacs |
| 2014/0168121 A1 | 6/2014 | Chou |
| 2014/0188121 A1 | 7/2014 | Lavallee |
| 2014/0207197 A1 | 7/2014 | Reisberg |
| 2014/0240355 A1 | 8/2014 | Isaacs |
| 2014/0244220 A1 | 8/2014 | McKinnon |
| 2014/0249591 A1 | 9/2014 | Peultier et al. |
| 2014/0260484 A1 | 9/2014 | Harper |
| 2014/0272881 A1 | 9/2014 | Barsoum |
| 2014/0275981 A1 | 9/2014 | Selover et al. |
| 2014/0278322 A1 | 9/2014 | Jaramaz |
| 2014/0284838 A1 | 9/2014 | Pfeffer et al. |
| 2014/0311203 A1 | 10/2014 | Crawford et al. |
| 2014/0364860 A1 | 12/2014 | Knoepfle et al. |
| 2014/0378828 A1 | 12/2014 | Penenberg et al. |
| 2015/0073265 A1 | 3/2015 | Popovic et al. |
| 2015/0100091 A1 | 4/2015 | Tohmeh |
| 2015/0150523 A1 | 6/2015 | Sirpad et al. |
| 2015/0157416 A1 | 6/2015 | Andersson |
| 2015/0216568 A1 | 8/2015 | Sanpera Trigueros et al. |
| 2015/0227679 A1 | 8/2015 | Kamer et al. |
| 2015/0238271 A1 | 8/2015 | Wollowick et al. |
| 2015/0282796 A1 | 10/2015 | Nawana et al. |
| 2015/0282797 A1 | 10/2015 | O'Neil |
| 2015/0328004 A1 | 11/2015 | Mafhouz |
| 2016/0100907 A1 | 4/2016 | Gomes |
| 2016/0117817 A1 | 4/2016 | Seel |
| 2016/0157751 A1 | 6/2016 | Mahfouz |
| 2016/0191887 A1 | 6/2016 | Casas |
| 2016/0210374 A1 | 7/2016 | Mosnier et al. |
| 2016/0220318 A1 | 8/2016 | Farardeau et al. |
| 2016/0235479 A1 | 8/2016 | Mosnier et al. |
| 2016/0235480 A1 | 8/2016 | Scholl |
| 2016/0242857 A1 | 8/2016 | Scholl |
| 2016/0262800 A1 | 9/2016 | Scholl et al. |
| 2016/0270772 A1 | 9/2016 | Beale |
| 2016/0296285 A1 | 10/2016 | Chaoui et al. |
| 2016/0354161 A1 | 12/2016 | Dietz |
| 2017/0071682 A1 | 3/2017 | Bar et al. |
| 2017/0119472 A1 | 5/2017 | Hermann et al. |
| 2017/0128145 A1 | 5/2017 | Hasser et al. |
| 2017/0135707 A9 | 5/2017 | Frey et al. |
| 2017/0135770 A1 | 5/2017 | Scholl |
| 2017/0165008 A1 | 6/2017 | Finley |
| 2017/0215857 A1 | 8/2017 | D'urso |
| 2017/0231710 A1 | 8/2017 | Scholl et al. |
| 2017/0252107 A1 | 9/2017 | Turner et al. |
| 2017/0252123 A1 | 9/2017 | D'urso |
| 2017/0258526 A1 | 9/2017 | Lang |
| 2017/0360493 A1 | 12/2017 | Zucker et al. |
| 2017/0367738 A1 | 12/2017 | Scholl et al. |
| 2018/0008349 A1 | 1/2018 | Gillman |
| 2018/0092699 A1 | 4/2018 | Finley |
| 2018/0098715 A1 | 4/2018 | Dietz |
| 2018/0104479 A1 | 4/2018 | Grill et al. |
| 2018/0116727 A1 | 5/2018 | Caldwell et al. |
| 2018/0132942 A1 | 5/2018 | Mosnier et al. |
| 2018/0228566 A9 | 8/2018 | McAfee |
| 2018/0233222 A1 | 8/2018 | Daley et al. |
| 2018/0253838 A1 | 9/2018 | Sperling et al. |
| 2018/0254107 A1 | 9/2018 | Casey et al. |
| 2018/0263701 A1 | 9/2018 | Casey et al. |
| 2018/0301213 A1 | 10/2018 | Zehavi et al. |
| 2018/0303552 A1 | 10/2018 | Ryan et al. |
| 2018/0310993 A1 | 11/2018 | Hobeika et al. |
| 2018/0368921 A1 | 12/2018 | Jeszenszky et al. |
| 2019/0029757 A1 | 1/2019 | Roh et al. |
| 2019/0046268 A1 | 2/2019 | Mosnier et al. |
| 2019/0046269 A1 | 2/2019 | Hedblom et al. |
| 2019/0069956 A1 | 3/2019 | Ryan et al. |

(56) References Cited

U.S. PATENT DOCUMENTS

| | | |
|---|---|---|
| 2019/0099221 A1 | 4/2019 | Schmidt et al. |
| 2019/0146458 A1 | 5/2019 | Roh et al. |
| 2019/0167435 A1 | 6/2019 | Cordonnier |
| 2019/0209212 A1 | 7/2019 | Scholl et al. |
| 2019/0216452 A1 | 7/2019 | Nawana et al. |
| 2019/0254750 A1 | 8/2019 | Metz |
| 2019/0254769 A1 | 8/2019 | Scholl et al. |
| 2019/0269459 A1 | 9/2019 | Mosnier et al. |
| 2019/0314094 A1 | 10/2019 | Crawford |
| 2019/0350657 A1 | 11/2019 | Tolkowsky |
| 2019/0362028 A1 | 11/2019 | Mosnier et al. |
| 2019/0380782 A1 | 12/2019 | McAfee et al. |
| 2019/0388099 A1 | 12/2019 | Zuhars et al. |
| 2020/0015857 A1 | 1/2020 | Rout et al. |
| 2020/0022758 A1 | 1/2020 | Shoham et al. |
| 2020/0038109 A1 | 2/2020 | Steinberg |
| 2020/0038111 A1 | 2/2020 | Turner et al. |
| 2020/0060768 A1 | 2/2020 | Mosnier et al. |
| 2020/0085503 A1 | 3/2020 | Casey et al. |
| 2020/0093542 A1 | 3/2020 | Arramon et al. |
| 2020/0093613 A1 | 3/2020 | Arramon et al. |
| 2020/0107883 A1 | 4/2020 | Herrmann et al. |
| 2020/0121394 A1 | 4/2020 | Mosnier et al. |
| 2020/0129217 A1 | 4/2020 | Zucker et al. |
| 2020/0129240 A1 | 4/2020 | Singh et al. |
| 2020/0138519 A1 | 5/2020 | Frey et al. |
| 2020/0155236 A1 | 5/2020 | Chi |
| 2020/0188026 A1 | 6/2020 | de Souza et al. |
| 2020/0197100 A1 | 6/2020 | Leung et al. |
| 2020/0202515 A1 | 6/2020 | Prasad et al. |
| 2020/0214854 A1 | 7/2020 | O'Grady |
| 2020/0222121 A1 | 7/2020 | Ignasiak |
| 2020/0261120 A1 | 8/2020 | Scholl |
| 2020/0268452 A1 | 8/2020 | Rezach et al. |
| 2020/0305985 A1 | 10/2020 | Tolkowsky |
| 2020/0311318 A1 | 10/2020 | Suddaby |
| 2020/0315708 A1 | 10/2020 | Mosnier et al. |
| 2020/0330160 A1 | 10/2020 | Dace et al. |
| 2020/0345420 A1 | 11/2020 | Hobeika et al. |
| 2020/0352651 A1 | 11/2020 | Junio et al. |
| 2020/0375636 A1 | 12/2020 | Hobeika et al. |
| 2020/0405397 A1 | 12/2020 | Liu et al. |
| 2020/0411163 A1 | 12/2020 | Zehavi et al. |
| 2021/0030443 A1 | 2/2021 | Scholl et al. |
| 2021/0038333 A1 | 2/2021 | Kostrzewski et al. |
| 2021/0059838 A1 | 3/2021 | Bodner |
| 2021/0093393 A1 | 4/2021 | Quist et al. |
| 2021/0145518 A1 | 5/2021 | Mosnier et al. |
| 2021/0145519 A1 | 5/2021 | Mosnier et al. |
| 2021/0153942 A1 | 5/2021 | Scheltienne et al. |
| 2021/0161682 A1 | 6/2021 | O'Neil et al. |
| 2021/0186615 A1 | 6/2021 | Shmayahu et al. |
| 2021/0210189 A1 | 7/2021 | Casey et al. |
| 2021/0212766 A1 | 7/2021 | Turner et al. |
| 2021/0216671 A1 | 7/2021 | Mosnier et al. |
| 2021/0244447 A1 | 8/2021 | Schroeder |
| 2021/0264601 A1 | 8/2021 | Pasha |
| 2021/0275227 A1 | 9/2021 | Park et al. |
| 2021/0298834 A1 | 9/2021 | Schlosser |
| 2021/0313062 A1 | 10/2021 | Junio |
| 2021/0315515 A1 | 10/2021 | Benson |
| 2021/0346092 A1 | 11/2021 | Redmond et al. |
| 2021/0346093 A1 | 11/2021 | Redmond et al. |
| 2022/0000556 A1 | 1/2022 | Casey et al. |
| 2022/0013211 A1 | 1/2022 | Steinberg et al. |
| 2022/0031396 A1 | 2/2022 | Ryan et al. |
| 2022/0096157 A1 | 3/2022 | Pollock et al. |
| 2022/0117754 A1 | 4/2022 | Sullivan et al. |
| 2022/0125602 A1 | 4/2022 | Zucker |
| 2022/0142709 A1 | 5/2022 | Zucker |
| 2022/0151699 A1 | 5/2022 | Schmidt et al. |
| 2022/0240986 A1 | 8/2022 | Scholl |

FOREIGN PATENT DOCUMENTS

| | | |
|---|---|---|
| CN | 200966629 | 10/2007 |
| CN | 101647724 | 2/2010 |
| CN | 202161397 | 3/2012 |
| CN | 202982181 | 6/2013 |
| CN | 107157579 | 9/2017 |
| CN | 107647914 | 2/2018 |
| CN | 109124763 A | 1/2019 |
| CN | 109124763 B | 9/2020 |
| DE | 9408154 | 7/1994 |
| DE | 29510041 | 10/1995 |
| DE | 29609276 | 8/1996 |
| DE | 10314882 | 10/2004 |
| DE | 102004008870 | 10/2004 |
| DE | 102007033219 | 1/2009 |
| DE | 102010033116 | 2/2012 |
| DE | 102011006574 | 10/2012 |
| DE | 202014100218 | 3/2014 |
| EP | 2017785 A1 | 1/2009 |
| EP | 2153785 | 2/2010 |
| EP | 2468201 | 6/2012 |
| EP | 2522295 A1 | 11/2012 |
| EP | 2730242 | 5/2014 |
| ES | 2401811 | 4/2013 |
| FR | 2975583 | 11/2012 |
| FR | 3004100 | 10/2014 |
| GB | 2267757 | 12/1993 |
| JP | H-04297270 | 10/1992 |
| JP | 2007213015 | 8/2007 |
| JP | 2007283081 | 11/2007 |
| JP | 2013230221 | 11/2013 |
| JP | 2015531661 | 11/2015 |
| JP | 2016093497 | 5/2016 |
| JP | 2016536051 | 11/2016 |
| PT | 103823 | 3/2009 |
| SU | 1747045 | 7/1992 |
| WO | 199808454 | 3/1998 |
| WO | 2007009263 A1 | 1/2007 |
| WO | 2009035358 | 3/2009 |
| WO | 2009039371 | 3/2009 |
| WO | 2009140294 A1 | 11/2009 |
| WO | 2011038845 | 4/2011 |
| WO | 2012062464 | 5/2012 |
| WO | 2012135653 A1 | 10/2012 |
| WO | 2013070628 | 5/2013 |
| WO | 2013085982 | 6/2013 |
| WO | 2013150233 | 10/2013 |
| WO | 2014016824 | 1/2014 |
| WO | 2014043661 | 3/2014 |
| WO | 2014055081 | 4/2014 |
| WO | 2014074850 | 5/2014 |
| WO | 2014088801 | 6/2014 |
| WO | 2014107144 | 7/2014 |
| WO | 2014143762 | 9/2014 |
| WO | 2015054543 | 4/2015 |
| WO | 2015195843 | 12/2015 |
| WO | 2017064719 | 4/2017 |
| WO | 2017127838 | 7/2017 |
| WO | 2021160599 | 8/2021 |

OTHER PUBLICATIONS

Lehman et al., "Do intraoperative radiographs in scoliosis surgery reflect radiographic result?", Clinical Orthopaedics and Related Research, 2010, pp. 679-686, 468, No. 2.

Aurouer et al., "Computerized preoperative planning for correction of sagittal deformity of the spine.", Surg Radiol Anat, 2009, pp. 781-792, 31, No. 10.

Farahani et al., "Prediction of the Movement Patterns for Human Squat Jumping Using the Inverse-Inverse Dynamics Technique", XIII International Symposium on Computer Simulation in Biomechanics, Jun. 30-Jul. 2, 2011, Leuven, Belgium, 2 pages.

Majdouline et al., "Computer simulation for the optimization of Instrumentation strategies in adolescent idiopathic scoliosis.", Med Biol Eng Comput, 2009, pp. 1143-1154, 47, No. 11.

Metz, Lionel N., et al., Computer-Assisted Surgical Planning and

(56) References Cited

OTHER PUBLICATIONS

Image-Guided Surgical Navigation in Refractory Adult Scoliosis Surgery, Spine vol. 33, No. 9, pp. E287-E292, 2008, Lippincott Williams & Wilkins.

Smith et al., "Clinical and radiographic evaluation of the adult spinal deformity patient", Neurosurg Clin N Am, 2013, pp. 143-156, 24, No. 2.

Tanquay et al., "Relation between the sagittal pelvic and lumbar spine geometries following surgical correction of adolescent idiopathic scoliosis", European Spine Journal, 2007, pp. 531-536, 16, No. 4.

Australian Exam Report in Application 2017225796, mailed Nov. 13, 2020, 5 pages.

Australian Exam Report in Application 2021203401, mailed Jan. 7, 2022, 3 pages.

European Extended Search Report in Application 17760840.3, mailed Sep. 30, 2019, 9 pages.

European Extended Search Report in Application 21168383.4, mailed Jun. 28, 2021, 8 pages.

Israeli Exam Report in Application 26132818, mailed Jun. 14, 2021, 3 pages.

Japanese 2nd Written Opinion in Application 2018-545412, mailed Jan. 17, 2022, 2 pages.

Japanese Decision of Refusal in Application 2018-545412, mailed Jun. 7, 2022, 3 pages.

Japanese Notice of Reasons for Refusal in Application 2018-545412, mailed Nov. 2, 2021, 6 pages.

Japanese Notice of Reasons for Refusal in Application 2018-545412, mailed Mar. 2, 2021, 8 pages.

Japanese Search Report in Application 2018-545412, mailed Feb. 15, 2021, 13 pages.

Japanese Written Opinion in Application 2018-545412, mailed Jun. 1, 2021, 3 pages.

K2M Pre-Bent Rod Tool video, located online at: https://www.youtube.com/watch?v=GE-UqEOFXFk, duration 3:50, uploaded by Surgimap on Feb. 16, 2017, last accessed on Sep. 12, 2022, 1 page.

Keops Demonstration Video, located online at: https://www.youtube.com/watch?v=5f_SoE6Ze8g, duration 5:11, uploaded by SMAIO69 on Nov. 29, 2012, last accessed on Sep. 12, 2022, 1 page.

Medicrea UNiD Spinal Rod Used at Scoliosis and Spinal Surgery video, located online at: https://www.youtube.com/watch?v=E-MonYoKSEg, duration 1:58, uploaded by John Henry Krause Voice Actor on Jul. 28, 2015, last accessed on Sep. 12, 2022, 3 pages.

PCT International Preliminary Report on Patentability in International Application PCT/US2017/020491, mailed Sep. 13, 2018, 7 pages.

PCT International Search Report and Written Opinion in International Application PCT/US2017/020491, mailed May 26, 2017, 10 pages.

Roussouly, Pierre et al., "Sagittal Parameters of the Spine: Biomechanical Approach", Eur. Spine J (Jul. 11, 2011); 20 (Suppl. 5):S578-S585.

Schlenk et al., "Biomechanics of spinal deformity", Neurosurgical Focus, 2003, 14, No. 1.

The NHS Innovations & EOS video, located online at: https://www.youtube.com/watch?v=GeU9kWcSY-I, duration 10:17, uploaded by EOS Imaging on Apr. 29, 2014, last accessed on Sep. 12, 2022, 9 pages.

Lionel N. Metz et. al., Computer-Assisted Surgical Planning and Image-Guided Surgical Navigation in Refractory Adult Scoliosis Surgery, Spine vol. 33, No. 9, pp. E287-E292, 2008, Lippincott Williams & Wilkins.

AnyBody Publication List, located online on Sep. 29, 2022 at: https://anybodytech.com/resources/anybodypublications/, 90 pages.

AnyBody Technology, "ARO Medical breaks the degenerative spiral", ARO Medical, Version 1.3, Nov. 20, 2013, 1 page.

AnyScript.org—Wiki: AnyScript Support Wiki, Main Page, located online on the Wayback Machine on Sep. 29, 2022 at: https://web.archive.org/web/2016022423555/http://wiki.anyscript.org:80/index.php/Main_Page, page last modified Oct. 5, 2015, 2 pages.

SPINAL BALANCE ASSESSMENT

CROSS REFERENCES TO RELATED APPLICATIONS

The present application is a continuation of U.S. patent application Ser. No. 16/692,209 filed on Nov. 22, 2019, which is a continuation of U.S. patent application Ser. No. 15/979,395 (now U.S. Pat. No. 9,968,408) filed on May 14, 2018, which is a continuation of U.S. patent application Ser. No. 14/216,411 (now U.S. Pat. No. 9,968,408) filed on Mar. 17, 2014, which claims priority to U.S. Provisional Application No. 61/802,180 filed on Mar. 15, 2013, the entire contents of which is hereby incorporated by reference into this disclosure as if set forth fully herein.

FIELD

The present invention relates to the field of corrective spinal surgery, including a system and associated methods for assessing the degree of balance and alignment achieved through corrective measures applied to the spine prior to completing the surgical procedure.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the sacral and coccygeal regions of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. Disruptions can be caused by any number factors including normal degeneration that comes with age, trauma, or various medical conditions. If a disruption to the spine becomes severe enough, damage to a nerve or part of the spinal cord may occur and can result in partial to total loss of bodily functions (e.g., walking, talking, breathing, etc.). Therefore, it is of great interest and concern to be able to treat and correct ailments of the spine.

When conservative efforts fail, treating spinal ailments very often includes a combination of spinal fusion and fixation. Generally, spinal fusion procedures involve removing some or all of an intervertebral disc, and inserting one or more intervertebral implants into the resulting disc space. Introducing the intervertebral implant serves to restore the height between adjacent vertebrae ("disc height") and maintain the height, and/or correct vertebral alignment issues, until bone growth across the disc space connects the adjacent vertebral bodies. During such procedures resection of ligaments and/or boney elements from the affected spinal area is common in order to access the disc space and/or decompress impinged nerve or spinal cord tissue. Though generally necessary to achieve the aims of the surgery, the resection of ligaments and/or boney tissue along the spine introduces instability (or, oftentimes, increased instability) to the spine.

Fixation systems are often surgically implanted during a fusion procedure to help stabilize the vertebrae to be fused until the fusion is complete or to address instabilities (either preexisting or created by the fusion or decompression procedure itself). Fixation constructs of various forms are well known in the art. Fixation systems usually use a combination of rods, plates, pedicle screws, and bone hooks to create a fixation construct across affected vertebrae. These fixations systems are designed to engage either the posterior elements (e.g. pedicle screw systems, spinous process plates) or anteriorly, the vertebral bodies (e.g. plates, anterior staple/rod systems). The configuration required for each procedure and patient varies due to the ailment being treated, the specific method of treatment (e.g. surgical approach, etc. . . . ) and the patient's specific anatomical characteristics. Like the fusion, the fixation system can be implanted across a single level or across multiple levels, and typically, the fixation system is positioned to span at least each level to be fused. In severe cases the fixation construct may stretch along the majority of the spine.

Despite the tremendous benefits gained by patients (e.g. a reduction or elimination of symptoms such as pain, poor posture, etc. . . . ) which can be credited to the fusion/fixation procedures, the procedures are not without disadvantages. For example, the loss of motion at one or more levels of the spine increases the loads placed on remaining untreated levels. These increased loads can hasten a breakdown at nearby untreated levels (commonly referred to as adjacent level disease), or, cause a hardware failure in which a portion of the spinal fixation construct breaks, generally leading to a failed fusion and instability. The importance of spinal balance as a determinant factor for positive surgical outcomes (those that avoid or limit the effects just described and result in a positive reduction of symptoms) is increasingly being recognized. Spinopelvic measurements have been identified as critical parameters to consider when evaluating overall balance. Several studies correlate worsening HRQL (Health Related Quality of Living) parameters with positive postoperative sagittal balance (defined as SVA>5 cm, PT>20°, PI≠LL±9°), where SVA=sagittal vertical axis, PT=pelvic tilt, and PI=pelvic incidence. Other relevant anatomical measurements include K=thoracic kyphosis, LL=lumbar lordosis, SA=sagittal alignment, CA=coronal alignment, T1-tilt. Tools to help the surgeon assess intraoperative changes in overall balance however are lacking. The tools and methods set forth herein are directed towards addressing these challenges.

DETAILED DESCRIPTION

The present application describes a balance assessment application that may be utilized by the surgeon before, during, and after surgery to ensure overall balance is achieved and maintained by the surgical procedure. The balance application includes a secure software package useable on portable computing devices (and preferably workstations as well) that manages patient data (images, relevant clinical information) and provides a platform for perioperative assessment and treatment. The application includes modules for preoperative, intraoperative, and postoperative surgical measurement of anatomy, as well as manipulation and reconstruction of collected images.

Figure 1:
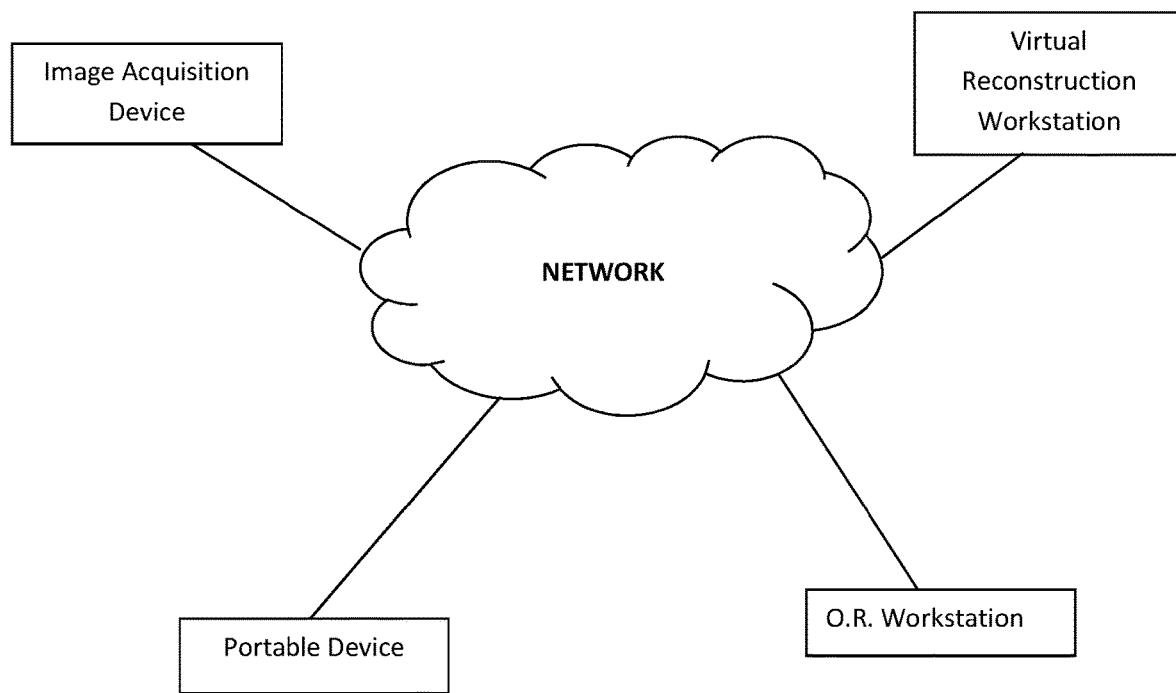
FIG. 1 is a flow chart depicting the network cloud structure utilized with the spinal balance assessment application described herein, according to one example embodiment.

With reference to FIG. 1, the balance assessment application utilizes a network structure (e.g. internet based cloud computing) that links a number of computer devices and diagnostic tools together over the internet. This structure enables secure data storage and transfer of diagnostic images for viewing on various computing devices (e.g. personal computers, tablets, or smart phones) and allows surgeons to access a patient's medical images at any time, with a variety of devices and on a variety of platforms to perform the clinical measurements for preoperative planning, intraoperative assessment and postoperative follow up. The surgeon can perform anatomical measurements directly on the mobile device, or on a separate workstation and then access the measurements later on the mobile device. The surgeon can also simulate the effects of surgical manipulations on postoperative alignment (e.g. simulate the effect of a 25° pedicle subtraction osteotomy) to maximize the surgeons ability to achieve overall balance. The balance assessment application may also utilize spatial mapping technology to evaluate intraoperative changes in alignment by tracking the location of anatomical landmarks. The spatial mapping technology may be similar to that described in U.S. patent application Ser. No. 13/815,643, filed Mar. 12, 2013 ("'643 Application"), which is incorporated herein by reference. It will be appreciated that the systems and software described in the Mar. 12, 2013 application may be used in conjunction with the spinal balance application described herein or may be integrated with the spinal balance application. It will also be appreciated that any of features, functions, tools, interfaces, etc. . . . described in the in the '643 Application may be utilized in the spinal balance application to accomplish the same or related goals (e.g. spinal measurements, virtual manipulations, virtual reconstructions, etc. . . . ).

Figure 2:
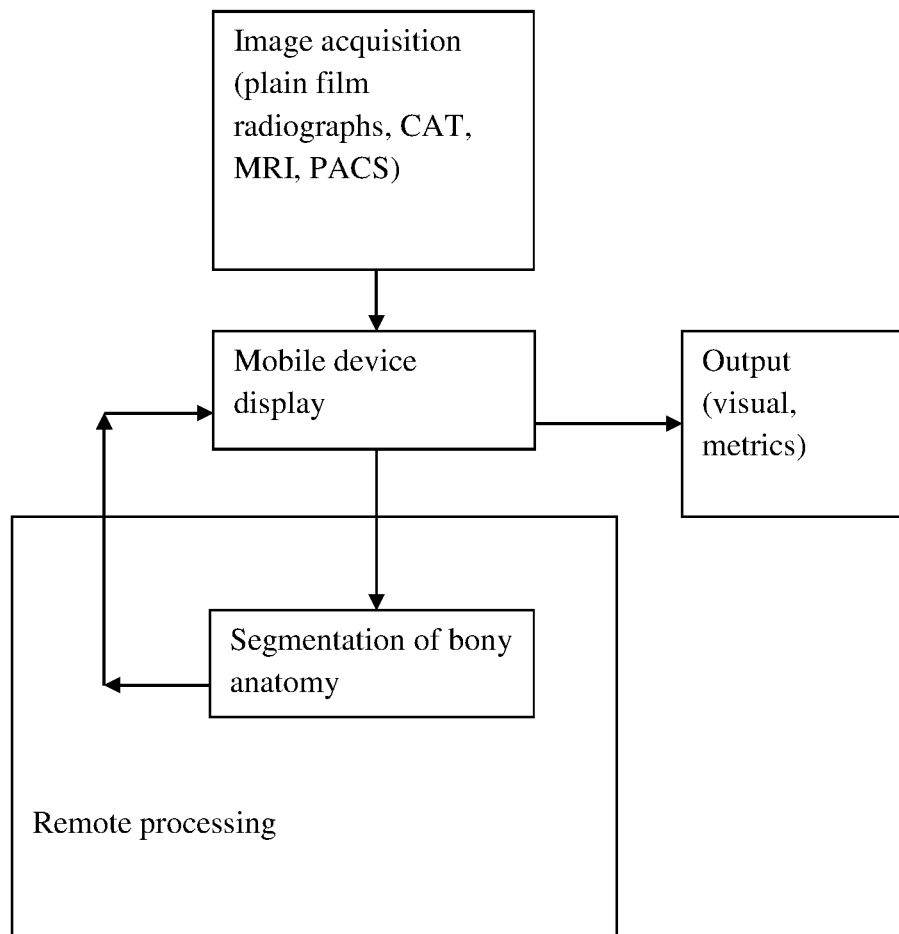
FIG. 2 is a flow chart depicting a preoperative module of the spinal balance assessment application described herein, according to one example embodiment.

The spinal balance application includes a preoperative module, a planning module, an intraoperative module, and postoperative module. With reference to FIG. 2, the preoperative module will now be described. The preoperative module begins with image acquisition. Pre-operative images (e.g. plain film radiographs, CAT, MRI, PACS) are acquired from the hospital, doctors office, archive, etc. . . . , and ported to the mobile device (e.g. laptop, tablet, smartphone) or other workstation. Optionally, the software package includes image recognition algorithms to detect bone in the images and automatically segments the bony anatomy such that the visual output only includes the bone structures. Metrics are performed on the bone structures to determine one or more of the anatomical measurements noted above. The metrics may be performed manually by the surgeon or assistant on a mobile device or workstation. By way of one example the software may include a GUI and the measurements may be calculated using the GUI. Still by way of example, the GUI may include the Virtual Protractor mode (or similar variation or modification) described in the '643 Application. Alternatively, the metrics may be calculated automatically by algorithms in the software.

Figure 3:
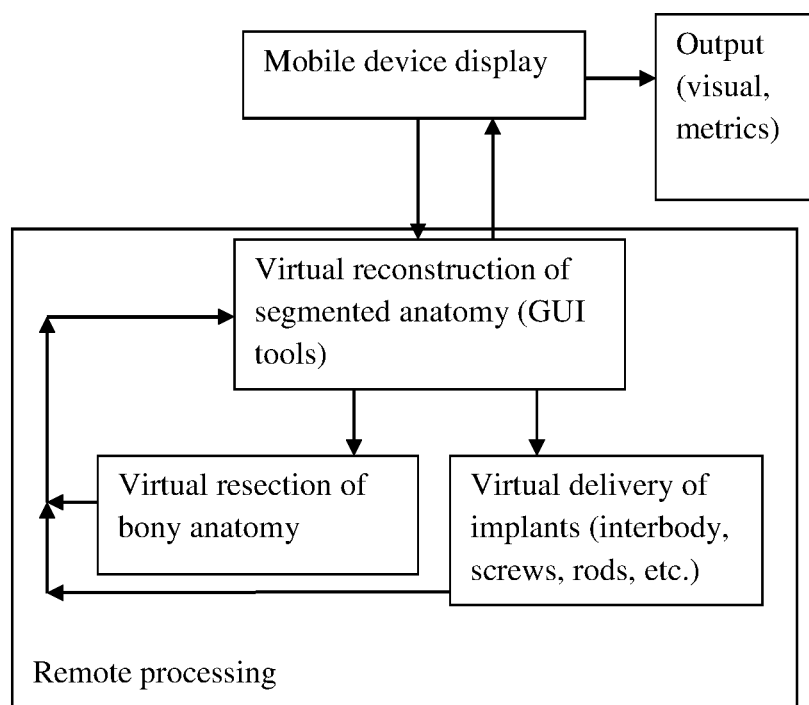
FIG. 3 is a flow chart depicting a surgical planning module of the spinal balance assessment application described herein, according to one example embodiment.

The surgical planning module is described now with reference to FIG. 3. Using the workstation (or mobile device if the processing power permits) a virtual reconstruction of the segmented anatomy may be performed. Using the GUI, the surgeon may resect boney anatomy, add implants (e.g. interbody devices, pedicle screws, rods, plates, etc. . . . ), and manipulate the position or alignment of anatomy. Metrics are performed to show the effects of the virtual surgery. Different degrees of manipulation, implant dimensions, and combinations thereof may be trialed until the desired correction and balance is achieved. The surgical plan (i.e. implant sizes, levels, resections, alignment manipulations, etc. . . . ) used to achieve the correction are saved for referral during the live surgery.

Figure 4:
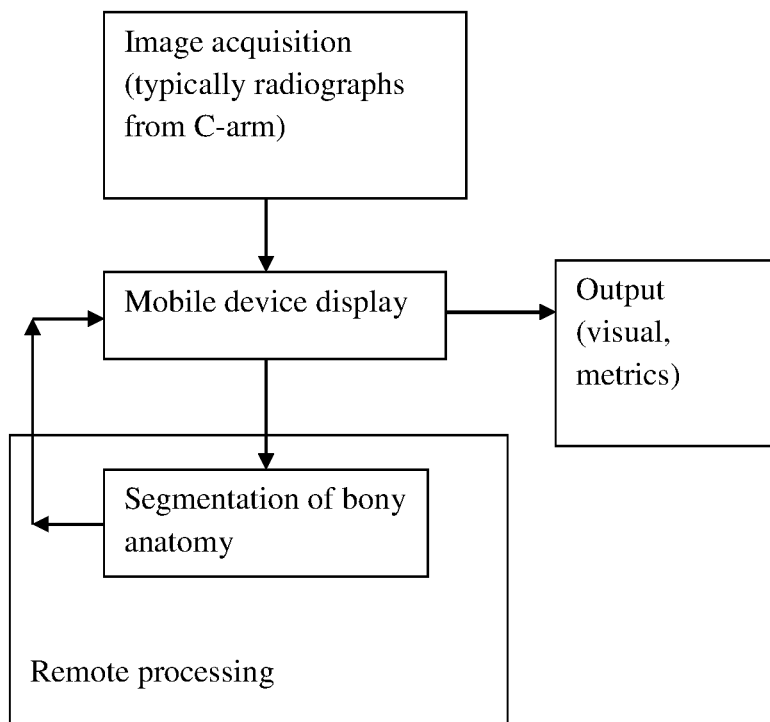
FIG. 4 is a flow chart depicting an intraoperative module of the spinal balance assessment application described herein, according to one example embodiment.

The intraoperative module is described with reference to FIG. 4. The intraoperative module begins with image porting of the surgical plan and preoperative imaging to the mobile device. Image acquisition (typically C-arm radiographs) occurs throughout the procedure as required and the images are ported to the mobile device or in O.R. workstation if available (it is noted that the processing system described in the '643 Application may be utilized as the in O.R. workstation). The images are automatically segmented to provide easier visualization. The surgical plan can be viewed on the mobile device and followed during the live surgery to attempt to achieve the same correction and balance. Metrics are performed (again either manually as noted above, or automatically by the software) to reconcile the actual output with the virtual output. If the actual output does not comport with the virtual output, the surgeon may continue the operation and adjust one or more parameters of the reconstruction. This process may be repeated until the appropriate correction and balance is obtained.

Figure 5:
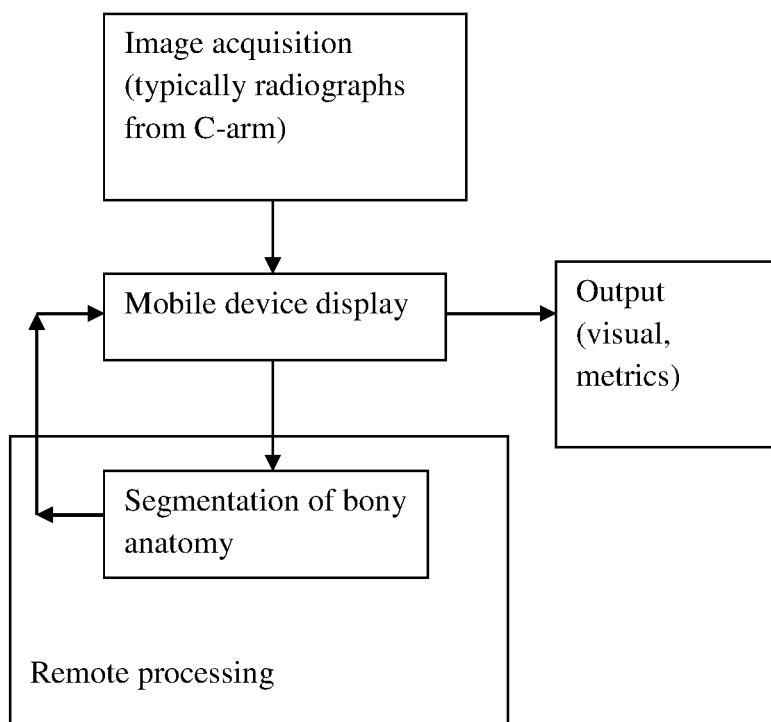
FIG. 5 is a flow chart depicting a postoperative module of the spinal balance assessment application described herein, according to one example embodiment.
Figure 6:
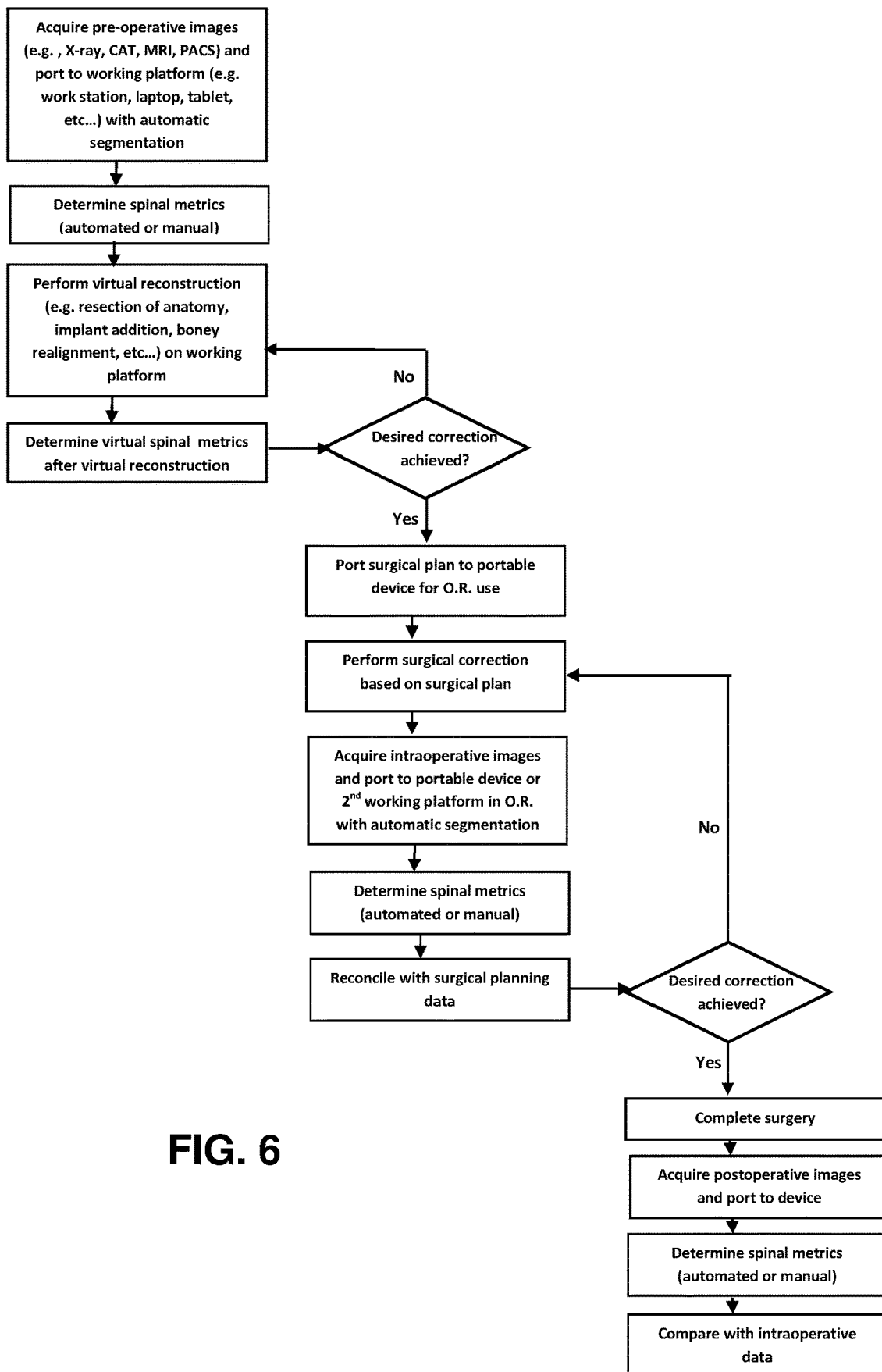
FIG. 6 is one example of a method for utilizing the spinal balance assessment application described herein for to ensure overall balance during a corrective spinal procedure.

The postoperative module is shown with reference to FIG. 5. The postoperative module is substantially similar to the preoperative module. However, in the postoperative module the postoperative metrics can be compared to the intraoperative metrics. This not only provides an ongoing assessment as to the overall balance of the spine, but it also provides data which can be collected and analyzed to aid in subsequent planning sessions. By way of example, FIG. 6 depicts one example method for using the spinal balance assessment application to ensure overall balance during a corrective spinal procedure.

While specific embodiments have been shown by way of example in the drawings and described herein in detail, it will be appreciated that the invention is susceptible to various modifications and alternative forms (beyond combining features disclosed herein). The description herein of specific embodiments is not intended to limit the invention to the particular forms disclosed, but on the contrary, the invention is to cover all modifications, equivalents, and alternatives falling within the spirit and scope of the invention.

What is claimed is:
1. A method comprising:
   determining, using a first computing device, a preoperative numeric value of at least one spinal metric from a preoperative image of a surgical site based on a pre- operative numeric relationship between two or more spinal landmarks that define the at least one spinal metric;

determining, using the first computing device, a desired reconstruction numeric value of the at least one spinal metric based on a virtual reconstruction of the surgical site;

performing a surgical correction on the surgical site based on the desired reconstruction numeric value or the virtual reconstruction;

determining, using a second computing device, an intraoperative numeric value of the at least one spinal metric from an intraoperative image of the surgical site based on an intraoperative numeric relationship between the two or more spinal landmarks;

reconciling, using the second computing device, the intraoperative numeric value of the at least one spinal metric from the intraoperative image with the desired reconstruction numeric value of the at least one spinal metric from the virtual reconstruction; and determining at least one spinal metric from a postoperative image and comparing the at least one spinal metric from the postoperative image with the at least one spinal metric from the intraoperative image.

2. The method of claim 1,
wherein the first computing device is a personal computer, a tablet, or a smart phone; and
wherein the second computing device is an operating room workstation.

3. The method of claim 1, wherein the virtual reconstruction includes anatomy resection, implant addition, or vertebral realignment.

4. The method of claim 1, further comprising:
segmenting, using a remote computing device, the preoperative image to form a segmented preoperative image; and
transmitting the segmented preoperative image to the first computing device.

5. The method of claim 1, further comprising:
segmenting, with the second computing device or a remote computing device, the intraoperative image to display only boney anatomy.

6. A method comprising:
with a first computing device:
determining a preoperative numeric value of at least one spinal metric from a preoperative image of a surgical site based on a preoperative numerical relationship between two or more anatomical landmarks that define the at least one spinal metric; and
determining a desired reconstruction numeric value of the at least one spinal metric based on a virtual reconstruction of the surgical site; and
with a second computing device:
assisting performance of a surgical correction on the surgical site based on the desired reconstruction numeric value;
determining an intraoperative numeric value of the at least one spinal metric from an intraoperative image of the surgical site based on an intraoperative numeric relationship between the two or more anatomical landmarks; and
reconciling the intraoperative numeric value of the at least one spinal metric from the intraoperative image with the desired reconstruction numeric value of the at least one spinal metric from the virtual reconstruction; and performing a surgical correction on the surgical site based on the desired reconstruction numeric value or the virtual reconstruction.

7. The method of claim 6,
wherein the first computing device is a personal computer, a tablet, or a smart phone; and
wherein the second computing device is an operating room workstation.

8. The method of claim 6, further comprising:
with one or more remote processors:
facilitating transfer of data from the first computing device to the second computing device.

9. The method of claim 6, further comprising:
with a third computing device:
providing a user interface via which a user can define the virtual reconstruction; and
interacting with the first computing device regarding the virtual reconstruction; and
wherein the third computing device is a personal computer, a tablet, or a smart phone.

10. A system comprising:
a first computing device configured to:
determine a preoperative numeric value of at least one spinal metric from a preoperative image of a surgical site based on a preoperative numerical relationship between two or more anatomical landmarks that define the at least one spinal metric; and
determine a desired reconstruction numeric value of the at least one spinal metric based on a virtual reconstruction of the surgical site; and
a second computing device configured to:
determine an intraoperative numeric value of the at least one spinal metric from an intraoperative image of the surgical site based on an intraoperative numeric relationship between the two or more anatomical landmarks; and
reconciling the intraoperative numeric value of the at least one spinal metric from the intraoperative image with the desired reconstruction numeric value of the at least one spinal metric from the virtual reconstruction; and
performing a surgical correction on the surgical site based on the desired reconstruction numeric value or the virtual reconstruction.

11. The system of claim 10,
wherein the first computing device is a personal computer, a tablet, or a smart phone; and
wherein the second computing device is an operating room workstation.

12. The system of claim 10, further comprising:
one or more remote processors configured to:
facilitate transfer of data from the first computing device to the second computing device.

13. The system of claim 10, further comprising:
one or more remote processors configured to:
segment anatomy in the preoperative image; and
provide the segmented anatomy to the first computing device.

14. The system of claim 10, further comprising:
a third computing device configured to:
provide a user interface via which a user can define the virtual reconstruction; and
interact with the first computing device regarding the virtual reconstruction; and
wherein the third computing device is a personal computer, a tablet, or a smart phone.

15. The system of claim 10, wherein the first or second computing device is configured to:
   determine at least one spinal metric from a postoperative image and comparing the at least one spinal metric from the postoperative image with the at least one spinal metric from the intraoperative image.

16. The system of claim 10, wherein the virtual reconstruction includes at least one of anatomy resection, implant addition, and vertebral realignment.

17. The system of claim 16, wherein the anatomy resection is a pedicle subtraction osteotomy.

18. The system of claim 10, wherein the second computing device is configured to:
   assist performance of a surgical correction on the surgical site based on the desired reconstruction numeric value.

19. The system of claim 10,
   wherein the at least one spinal metric includes one or more of the following spinal metrics: sagittal vertical axis, pelvic tilt, pelvic incidence, thoracic kyphosis, lumbar lordosis, sagittal alignment, coronal alignment, or tilt.

20. The system of claim 10, wherein the first computing device is further configured to receive user input measuring the at least one spinal metric.

* * * * *